US008802724B2

(12) United States Patent
Ghosh et al.

(10) Patent No.: US 8,802,724 B2
(45) Date of Patent: Aug. 12, 2014

(54) PROCESSES AND INTERMEDIATES FOR PREPARING SUBSTITUTED HEXAHYDROFURO [2,3-B] FURANS

(75) Inventors: Arun K. Ghosh, West Lafayette, IN (US); Cuthbert D Martyr, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/990,558

(22) PCT Filed: Nov. 30, 2011

(86) PCT No.: PCT/US2011/062611
§ 371 (c)(1),
(2), (4) Date: Aug. 9, 2013

(87) PCT Pub. No.: WO2012/075122
PCT Pub. Date: Jun. 7, 2012

(65) Prior Publication Data
US 2013/0338380 A1    Dec. 19, 2013

Related U.S. Application Data

(60) Provisional application No. 61/418,123, filed on Nov. 30, 2010.

(51) Int. Cl.
*A61K 31/34*    (2006.01)
*C07D 493/04*   (2006.01)
*C07D 317/20*   (2006.01)
*C07D 317/30*   (2006.01)
*C07D 317/22*   (2006.01)

(52) U.S. Cl.
CPC ............ *C07D 493/04* (2013.01); *C07D 317/20* (2013.01); *C07D 317/30* (2013.03); *C07D 317/22* (2013.01)

USPC .......................................... 514/470; 549/464

(58) Field of Classification Search
USPC ........................... 549/454, 464, 453; 514/470
See application file for complete search history.

(56) References Cited

U.S. PATENT DOCUMENTS

| 7,126,015 | B2 | 10/2006 | Kesteleyn et al. |
| 7,468,448 | B2 | 12/2008 | Ikemoto et al. |
| 2010/0113582 | A1 | 5/2010 | Ghosh |
| 2011/0118330 | A1 | 5/2011 | Ghosh |
| 2012/0059161 | A1 | 3/2012 | Ghosh |

FOREIGN PATENT DOCUMENTS

| WO | WO 2006089942 A1 * | 8/2006 | ........... C07D 493/04 |
| WO | WO 2008/133234 | 11/2008 | |
| WO | WO 2010/006050 | 1/2010 | |
| WO | WO 2010/132494 | 11/2010 | |

OTHER PUBLICATIONS

PCT Search Report and Written Opinion for PCT/US2011/062611, completed Apr. 9, 2012.
Chan, Ka-Kong, et al., "Transfer of Chirality in the [2,3] Sigmatropic Rearrangement of Allylic Alcohols to β,γ-Unsaturated Amides, Preparation of Optically Active Nine- and Fourteen-Carbon Saturated Isoprenoid Synthons,", 1977, J. Org. Chem., vol. 42, No. 24, pp. 3828-3832.
"International Application Serial No. PCT/US2011/062611, International Preliminary Report on Patentability mailed Mar. 6, 2014", 5 pgs.

* cited by examiner

*Primary Examiner* — Kristin Vajda
(74) *Attorney, Agent, or Firm* — Schwegman, Lundberg & Woessner, P.A.

(57) ABSTRACT

The invention described herein pertains to processes and compounds useful in the preparation of bis-tetrahydrofurans. The invention described herein also pertains to compounds useful for treating HIV infections.

17 Claims, No Drawings

PROCESSES AND INTERMEDIATES FOR PREPARING SUBSTITUTED HEXAHYDROFURO [2,3-B] FURANS

CROSS REFERENCE TO RELATED APPLICATIONS

This application is a national stage under 35 USC §371(b) of International Application No. PCT/US2011/062611, filed Nov. 30, 2011, which claims the benefit under 35 USC §119 (e) of U.S. Provisional Application Ser. No. 61/418,123 filed on Nov. 30, 2010, the entire disclosures of which are incorporated herein by reference.

GOVERNMENT RIGHTS

This invention was made with government support under GM053386 awarded by the National Institutes of Health. The government has certain rights in the invention.

TECHNICAL FIELD

The invention described herein pertains to processes and compounds useful in the preparation of bis-tetrahydrofurans. The invention described herein also pertains to compounds useful for treating HIV infections.

BACKGROUND AND SUMMARY

In recent years, the bis-tetrahydrofuranyl ligand has become an important ligand in the design of HIV-protease inhibitors. Since its discovery, it has been the salient feature in many drug candidates. Darunavir, (1), the first FDA approved second generation protease inhibitor, is currently being used in the treatment of naïve and drug resistant HIV. Since its approval, Brecanavir, (2) and GSK-8374, (3) have also capitalized on this moiety.

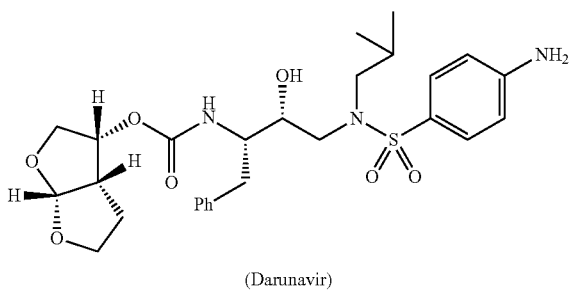

(Darunavir)

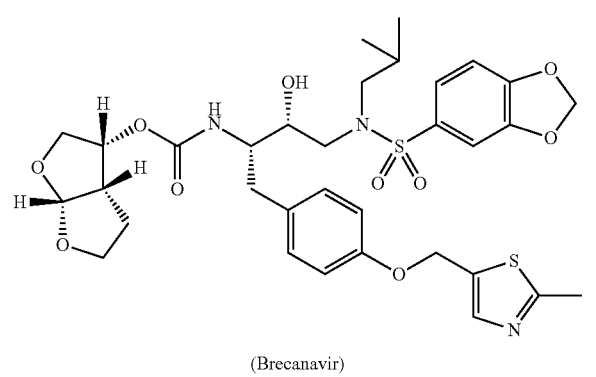

(Brecanavir)

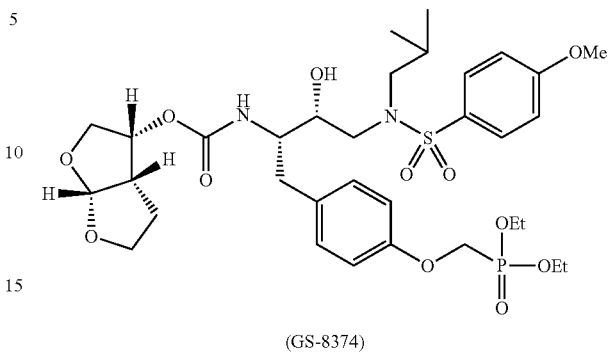

(GS-8374)

There have been several syntheses for the bis-THF ligand (a. Ghosh, A. K.; et al.; *Tetrahedron Letters,* 1995, 36, 505-508. (b) Doan, B. D.; et al.; WO 03/024974 A2. (c) A. K. Ghosh et al. *Tetrahedron Letters,* 1999, 40, 1083-1086. (d) Lemaire, S. F. E.; et al.; WO/2008/055970; the disclosure of each of the foregoing publications, and each additional publication cited herein, is incorporated herein in its entirety by reference. A method utilizing a photochemical irradiation with 1,3-dioxolane to give the key intermediate in good diastereomeric ratios has been reported (Ghosh, A. K., et al., M. *J. Org. Chem.* 2004, 69, 7822-7829). Use of an asymmetric anti-aldol condensation to obtain the key intermediate needed to obtain the bis-THF ligand has also been described (Ghosh, A. K., et al., *Synthesis,* 2006, 3015-3018). Two chiral syntheses have been reported, both of which include a conjugate addition of nitromethane (Quaedflieg, P. J. L. M., et al., *Org. Lett.* 2005, 7, 5917-5920). Other syntheses have been attempted with the use of various catalysts to obtain the desired product (Black, D. M., et al., *Tetrahedron: Asymmetry,* 2008, 19, 2015-2019). However, many of the previously disclosed methods require late-stage resolution to obtain the enantiomerically pure ligand. Accordingly, alternative processes for preparing this important ligand in second generation protease inhibitors in the treatment of HIV are useful.

DETAILED DESCRIPTION

Illustrative embodiments of the invention are described by the following enumerated clauses:

1. A process for preparing a compound containing a bis-tetrahydrofuran, the process comprising the step of (a) contacting a compound of formula (I)

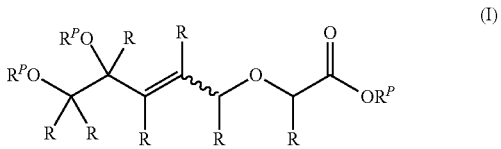

with a base to provide a compound of formula (II)

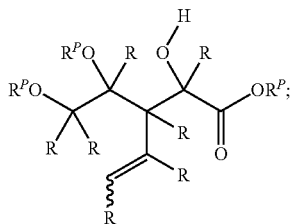

(II)

or (b) inverting the stereochemistry of a compound of formula (II) at the (*) carbon to provide a compound of formula (II*)

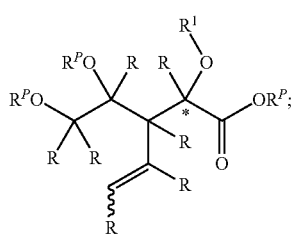

(II*)

or (b) reducing a compound of formula (II) or formula (II*) with a reducing agent to provide a compound of formula (III)

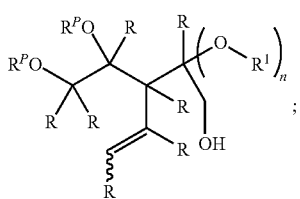

(III)

or (c) oxidizing a compound of formula (III) with an oxidizing agent to provide a compound of formula (IV)

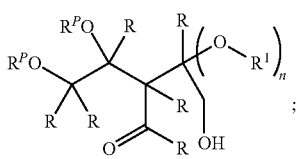

(IV)

or any combination of two or more of the foregoing steps (a), (b), (c), and (d); wherein n is 0 or 1;

R in each instance is independently selected from the group consisting of hydrogen, and alkyl, alkenyl, alkynyl, cycloalkyl, cycloalkenyl, heteroalkyl, heteroalkenyl, cyclo-heteroalkyl, cycloheteroalkenyl, aryl, heteroaryl, arylalkyl, and heteroarylalkyl, each of which is optionally substituted; or independently geminal pairs of R are taken together to form an optionally substituted carbocycle or optionally substituted heterocycle; or independently vicinal pairs of R are taken together to form an optionally substituted carbocycle or optionally substituted heterocycle;

$R^P$ in each instance is an independently selected OH protecting group; and $R^1$ is hydrogen or an OH protecting group, or is selected from the group consisting of alkyl, alkenyl, alkynyl, cycloalkyl, cycloalkenyl, heteroalkyl, heteroalkenyl, cyclo-heteroalkyl, cycloheteroalkenyl, aryl, heteroaryl, arylalkyl, and heteroarylalkyl, each of which is optionally substituted.

2. The process of clause 1 wherein the compound of formula (I) is

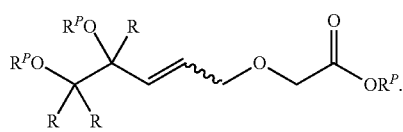

3. The process of clause 1 wherein the compound of formula (I) is

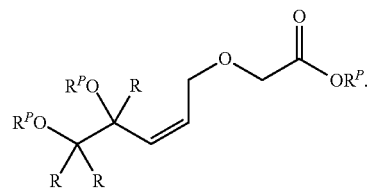

4. The process of clause 1 wherein the compound of formula (I) is

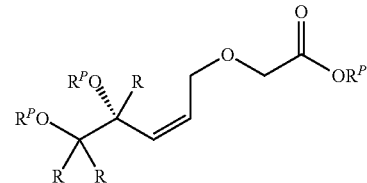

or the enantiomer thereof.

5. The process of any one of the foregoing clauses wherein the compound of formula (II) is

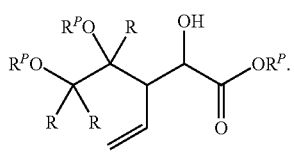

6. The process of any one of the foregoing clauses wherein the compound of formula (II) is

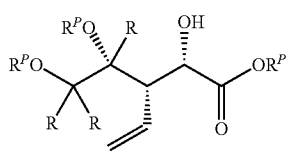

or the enantiomer thereof.

7. The process of any one of the foregoing clauses wherein the compound of formula (II*) is

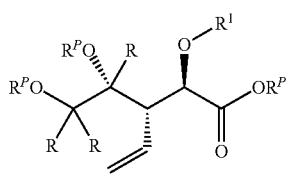

or the enantiomer thereof.

8. The process of any one of the foregoing clauses wherein the compound of formula (III) is

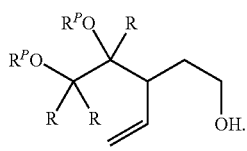

9. The process of any one of the foregoing clauses wherein the compound of formula (III) is

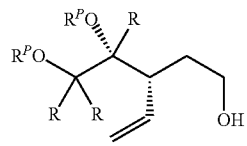

or the enantiomer thereof.

10. The process of any one of the foregoing clauses wherein the compound of formula (III) is

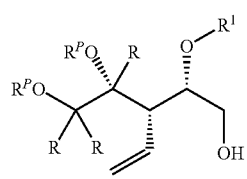

or the enantiomer thereof.

11. The process of any one of the foregoing clauses wherein the compound of formula (III) is

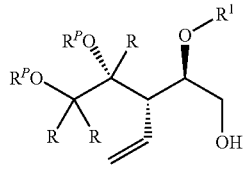

or the enantiomer thereof.

12. The process of any one of the foregoing clauses wherein the compound of formula (IV) is

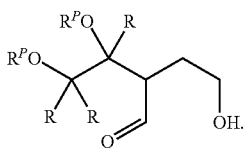

13. The process of any one of the foregoing clauses wherein the compound of formula (IV) is

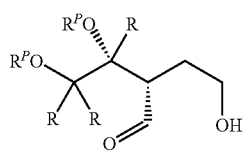

or the enantiomer thereof.

14. The process of any one of the foregoing clauses wherein the compound of formula (IV) is

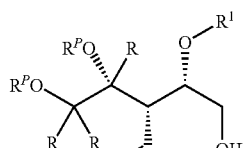

or the enantiomer thereof.

15. The process of any one of the foregoing clauses wherein the compound of formula (IV) is

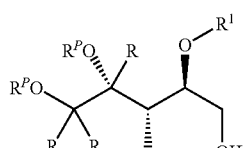

or the enantiomer thereof.

16. The process of any one of clauses 1-15 wherein the base is a lithium alkoxide, a sodium alkoxide, a potassium alkoxide, a lithium amide, a sodium amide, a magnesium amide, or a potassium amide.

17. The process of any one of clauses 1-16 wherein the inverting step includes converting the free hydroxyl to an ester of a carboxylic acid.

18. The process of any one of clauses 1-17 wherein the reducing agent is selected from the group consisting of a lithium hydridoaluminate and a sodium hydridoaluminate.

19. The process of any one of clauses 1-18 wherein the reducing agent is lithium aluminum hydride or sodium bis(2-methoxyethoxo)dihydridoaluminate.

20. The process of any one of clauses 1-19 wherein the base is potassium t-butoxide, sodium t-amyloxide, or lithium hexamethyldisilazide.

21. The process of any one of clauses 1-20 wherein the oxidizing agent is selected from the group consisting of ozone, $NaIO_4$—$RuO_4$, and $NaIO_4$—$OsO_4$.

22. The process of any one of clauses 1-21 wherein the oxidizing agent is ozone.

23. The process of any one of clauses 1-22 wherein step (a) is conducted at a temperature of from about −50° C. to about 0° C.; from about −40° C. to about 10° C.; from about −40° C. to about −20° C.; from about −30° C. to about −20° C.; from about −20° C. to about −10° C.; from about −10° C. to about 0° C.; or at ambient temperature.

23a. The process of any one of the clauses 1-23 wherein the compound containing a bis-tetrahydrofuran has the formula

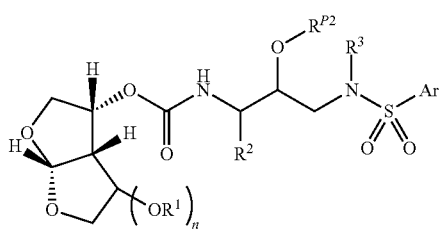

wherein n is 0 or 1; $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; $R^2$ is alkyl, cycloalkyl, heteroalkyl, cycloheteroalkyl, arylalkyl, or heteroalkyl, each of which is optionally substituted; $R^{P2}$ is hydrogen, hydroxyl protecting group or a pro-drug forming group; $R^3$ is alkyl, heteroalkyl, cycloalkyl, cycloheteroalkyl, arylalkyl, or heteroarylalkyl; and Ar is aryl or heteroaryl, each of which is optionally substituted.

23b. The process of clause 23a wherein $R^2$ is arylalkyl.

23c. The process of clause 23a or 23b wherein $R^2$ is benzyl.

23d. The process any one of clauses 23a-23c wherein $R^3$ is branched alkyl.

23e. The process any one of clauses 23a-23d wherein $R^3$ is iso-butyl.

23f. The process any one of clauses 23a-23e wherein $R^{P2}$ is hydrogen.

23g. The process any one of clauses 23a-23f wherein Ar is substituted phenyl.

23h. The process any one of clauses 23a-23g wherein $R^1$ is alkyl or arylalkyl.

23i. The process any one of clauses 23a-23h wherein $R^1$ methyl or benzyl.

23j. The process any one of clauses 23a-23i wherein Ar is phenyl substituted on the 4 position with OMe, $CH_2OMe$, $NH_2$, or Ar is 3,4-methylenedioxyphenyl.

23k. The process any one of clauses 23a-23j wherein n is 0.

23l. The process any one of clauses 23a-23j wherein n is 1.

24. A compound of formula (I)

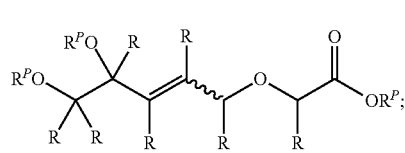

or a compound of formula (II)

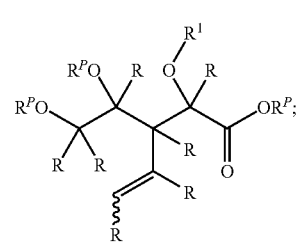

or a compound of the formulae

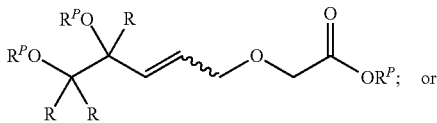

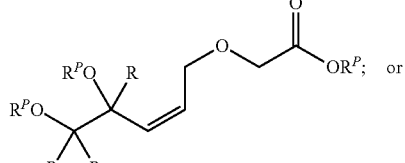

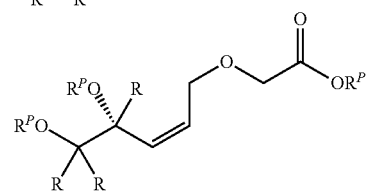

or the enantiomer thereof; or

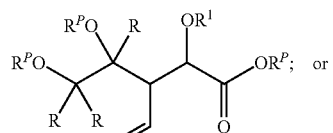

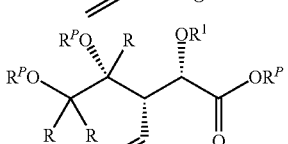

or the enantiomer thereof; or

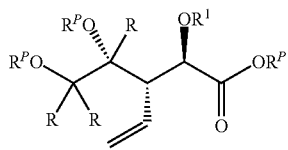

or the enantiomer thereof; or

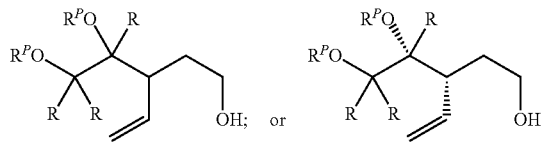

or the enantiomer thereof; or

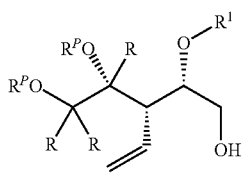

or the enantiomer thereof; or

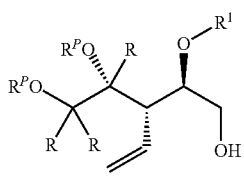

or the enantiomer thereof; or

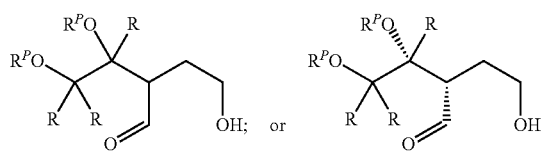

or the enantiomer thereof; or

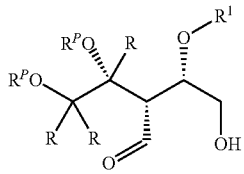

or the enantiomer thereof; or

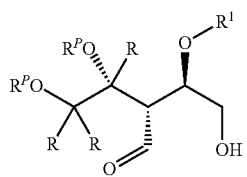

or the enantiomer thereof; wherein

R in each instance is independently selected from the group consisting of hydrogen and alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; or independently geminal pairs of R are taken together to form an optionally substituted carbocycle or optionally substituted heterocycle; or independently vicinal pairs of R are taken together to form an optionally substituted carbocycle or optionally substituted heterocycle;

$R^P$ in each instance is an independently selected OH protecting group; and $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted.

25. The process or compound of any one of the previous clauses wherein each R is hydrogen.

26. The process or compound of any one of the previous clauses wherein at least one of R is not hydrogen.

26a. The process or compound of any one of the previous clauses wherein one of R is not hydrogen.

27. A compound having the formula

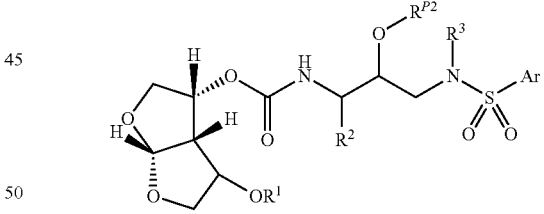

wherein $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; $R^2$ is alkyl, cycloalkyl, heteroalkyl, cycloheteroalkyl, arylalkyl, or heteroalkyl, each of which is optionally substituted; $R^{P2}$ is hydrogen, hydroxyl protecting group or a pro-drug forming group; $R^3$ is alkyl, heteroalkyl, cycloalkyl, cycloheteroalkyl, arylalkyl, or heteroarylalkyl; Ar is aryl or heteroaryl, each of which is optionally substituted; and wherein the compound is not

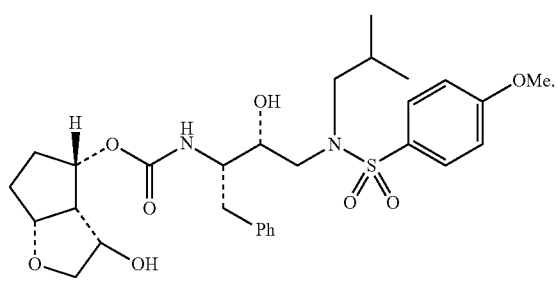

28. The compound of clause 27 wherein $R^2$ is arylalkyl.

29. The compound of clause 27 or 28 wherein $R^2$ is benzyl.

30. The compound any one of clauses 27-29 wherein $R^3$ is branched alkyl.

31. The compound any one of clauses 27-30 wherein $R^3$ is iso-butyl.

cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted;

35. The compound any one of clauses 27-32 wherein $R^1$ is alkyl or arylalkyl.

36. The compound any one of clauses 27-32 wherein $R^1$ methyl or benzyl.

37. The compound any one of clauses 27-36 wherein Ar is phenyl substituted on the 4 position with OMe, $CH_2OMe$, $NH_2$, or Ar is 3,4-methylenedioxyphenyl.

38. A pharmaceutical composition comprising the compound of any one of clauses 27-37; and one or more carriers, diluents, or excipients, or a combination thereof.

39. A method of treating a patient in need of relief from HIV infection comprising the step of administering to the patient a therapeutically effective amount of the compound of any one of the clauses 27-37 or the composition of clause 38.

In another embodiment, the following processes and compounds are described herein

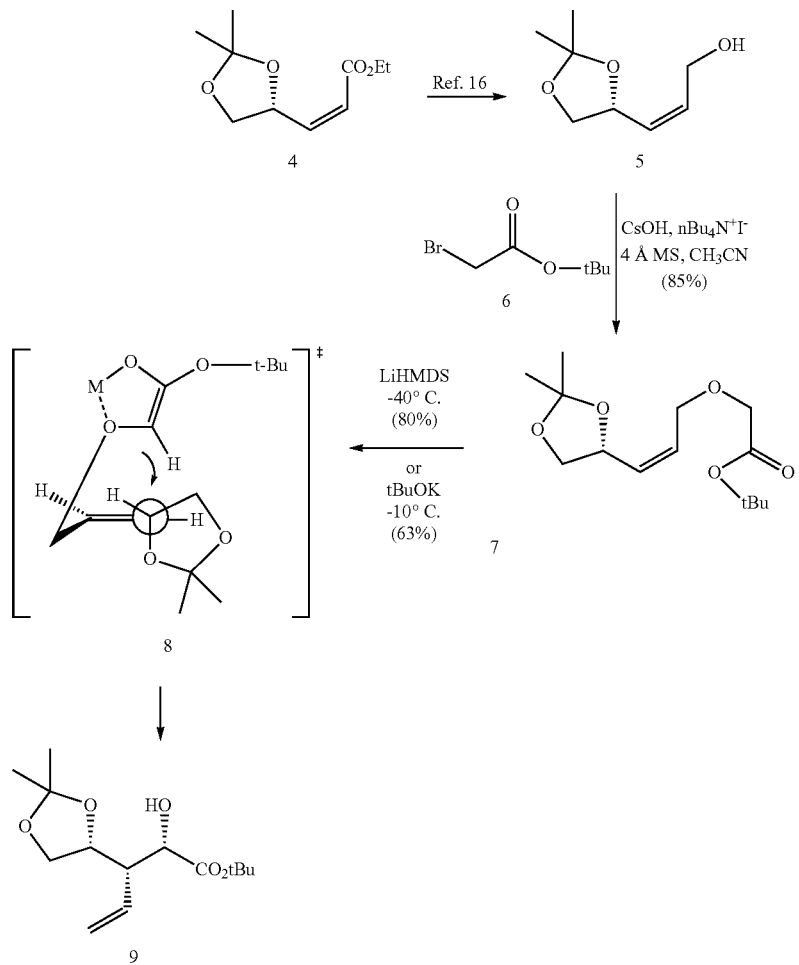

32. The compound any one of clauses 27-31 wherein $R^{P2}$ is hydrogen.

33. The compound any one of clauses 27-32 wherein Ar is substituted phenyl.

34. The compound any one of clauses 27-32 wherein $R^1$ is selected from the group consisting of alkyl, alkenyl, alkynyl, Diisobutyl aluminum hydride (Dibal-H) reduction of 4 resulted in alcohol 5 (Scheme 1). It was found that the O-alkylation of 5 with t-butyl bromoacetate proceeds under a variety of conditions. Several conditions for the alkylation are shown in Table 1. The use of KOtBu in THF resulted in a single product in a yield of 56%. The use of $Cs_2CO_3$ in DMF proceeded with a yield of 59%. In addition, unreacted starting material and a transesterified side product were isolated. Use of CsOH—H$_2$O and activated molecular sieves, in the presence of tetrabutylammonium iodide in acetonitrile provided the O-alkylated product 7 in a yield of 85%. Under these conditions, only a small amount of the transesterification product (<5%) and a small amount (<5%) of starting material were recovered.

TABLE 1

Conditions for O-alkylation

| Entry | Base | Solvent | Time | % yield |
|---|---|---|---|---|
| 1 | KOtBu | THF | 2 h | 56 |
| 2 | NaH | DMF | 6 h | 60 |
| 3 | Cs$_2$CO$_3$ | DMF | 24 h | 59 |
| 4 | Cs$_2$CO$_3$ | CH$_3$CN | 24 h | 70 |
| 5 | CsOH—H$_2$O | CH$_3$CN | 48 h | 85 |

The [2,3]-sigmatropic rearrangement proceeds under a variety of conditions as shown in Table 2. Reaction with KOtBu at 23° C. provided a 4:1 diastereoselective ratio at the C2-chiral center. Lowering the reaction temperature to −10° C. resulted in an increase in selectivity (17:1). In both cases, the isolated yields were approximately 60%. Because the C2-chiral center could be eliminated en route to the bis-THF ligand, other conditions were explored. Reaction with LiHMDS in THF at −20° C. provided 9 in 55% yield and 6:1 diastereoselectivity. The same reaction conducted in the temperature range of −40° C. to −30° C. for 1 h provided diastereomer 9 as a single product in 80% yield. Without being bound by theory, it is believed that the stereochemical outcome of the [2,3]-sigmatropic rearrangement can be rationalized by a proposed transition-state model 8 in which the allylic C—O bond of the 1,3-dioxolane is orthogonal to the plane of the allylic C═C and is antiperiplanar with respect to the approaching carbanion.

TABLE 2

Reaction Conditions for the rearrangement

| Entry | Base | Temp (° C.) | Time | % yield (dr) |
|---|---|---|---|---|
| 1 | KOtBu | 23° C. | 15 min | 60% (4:1) |
| 2 | KOtBu | −10° C. | 1 h | 63% (17:1) |
| 3 | LiHMDS | −20° C. | 1 h | 55% (6:1) |
| 4 | LiHMDS | −40° C. to −30° C. | 1 h | 80% (99:1) |

In another embodiment, the following processes and compounds are described herein Scheme 2. Synthesis of bis-THF ligand 11

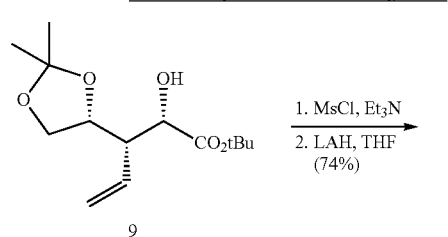

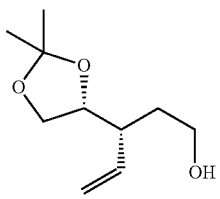

10

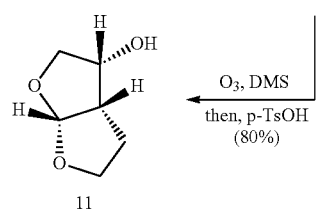

11

Alcohol 9 was converted to the corresponding mesylate. LAH reduction of the mesylate provided alcohol 10 in 74% yield over 2 steps (Scheme 2). Oxidative cleavage of the terminal alkene followed by acid catalyzed cyclization, in the presence of a catalytic amount of p-TsOH in CHCl$_3$ at reflux afforded the bis-THF alcohol 11 in 80% yield.

In another embodiment, the following processes and compounds are described herein Scheme 3. Syntheses of substituted bis-THF ligands

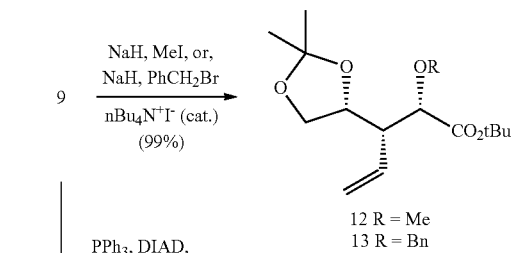

12 R = Me
13 R = Bn

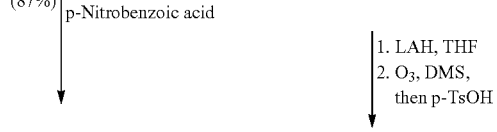

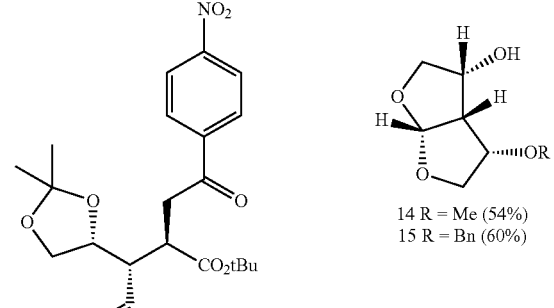

14 R = Me (54%)
15 R = Bn (60%)

16

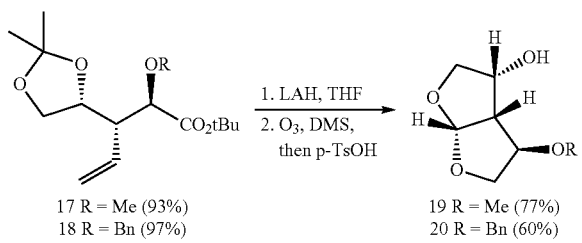

17 R = Me (93%)
18 R = Bn (97%)

19 R = Me (77%)
20 R = Bn (60%)

As shown in Scheme 3, rearrangement product 9 is useful for the synthesis of substituted bis-THF ligands. Alcohol 9 can be functionalized into derivatives which can further interact with the HIV-1 protease backbone atoms. In one embodiment, reaction of the free hydroxyl group provided methyl and benzyl and ethers 12 and 13, respectively. It is appreciated that other chemical modifications of the free hydroxyl group are possible resulting in additional derivatives. LAH reduction, followed by ozonolysis and acid catalyzed cyclization resulted in compounds 14 and 15, respectively. Inversion of the C2-hydroxyl group of 9 using Mitsunobu's protocol gave 16 in 87% yield. Selective deprotection of the nitro benzoate with potassium carbonate in methanol at 0° C. and subsequent reaction with methyl iodide or benzyl bromide provided methyl and benzyl ethers 17 and 18, respectively. LAH reduction, ozonolysis, and cyclization resulted in the substituted bis-THF ligands 19 and 20.

In another embodiment, the following processes and compounds are described herein

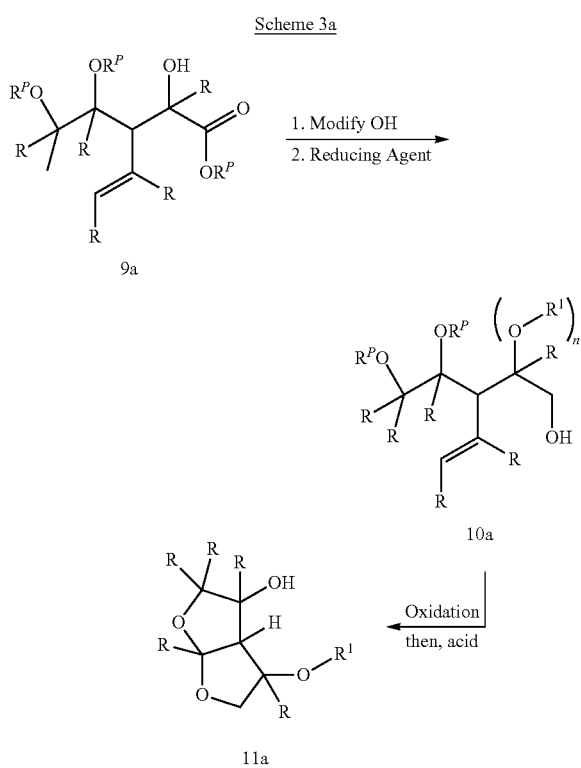

In another embodiment, the following processes and compounds are described herein Scheme 4. Synthesis of protease inhibitors

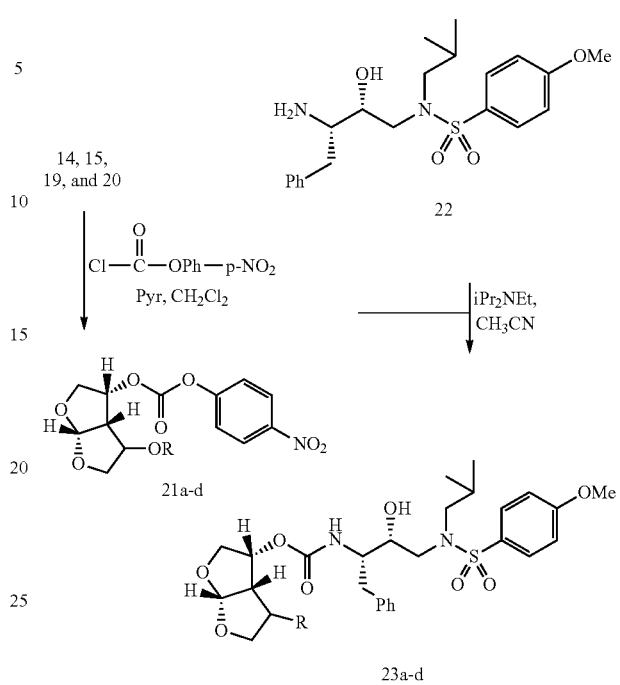

As shown in Scheme 4, alcohols 14, 15, 20, and 21 were activated with p-nitrophenyl chloroformate to provide mixed activated carbonates 21a-d. These carbonates were reacted with amine 22 to afford HIV-1 protease inhibitors 23a-d. These inhibitors were evaluated for their activity in both enzyme inhibitory and antiviral assays. The results are shown in Table 3. The enzyme inhibitory activity ($K_i$) was determined according to an assay protocol reported by Toth and Marshall (Toth, M. V.; Marshall, G. R. *Int. J. Pep. Protein Res.* 1990, 36, 544-550). The inhibitors displayed potent enzyme inhibitory activity. Compound 23c ($K_i$=0.0029 nM) is the most potent compound in this series. Its diastereomer 23a (Ki=0.05 nM) displayed a lower enzyme inhibitory activity. The benzyl derivatives 23b and 23d have also showed lower enzyme activity. Antiviral $IC_{50}$ values were determined using the MTT assay (Koh, Y., et al., *Antimicrob. Agents Chemother.* 2003, 47, 3123-3129.). Consistent with its enzyme inhibitory potency, inhibitor 23c exhibited an impressive antiviral activity ($IC_{50}$=2.4 nM).

In another embodiment, compounds are described having the formula IIa

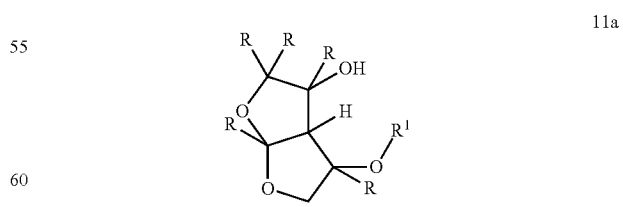

wherein R in each instance is independently selected from the group consisting of hydrogen and alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted;

or independently geminal pairs of R are taken together to form an optionally substituted carbocycle or optionally substituted heterocycle; or independently vicinal pairs of R are taken together to form an optionally substituted carbocycle or optionally substituted heterocycle;

$R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted; and wherein the compound is not

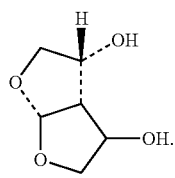

In another embodiment, compounds are described having the formula

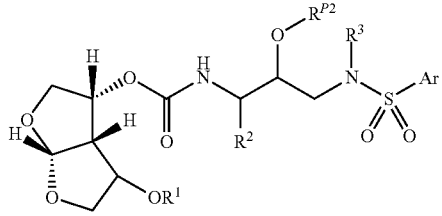

wherein $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; $R^2$ is alkyl, cycloalkyl, heteroalkyl, cycloheteroalkyl, arylalkyl, or heteroalkyl, each of which is optionally substituted; $R^{P2}$ is hydrogen, hydroxyl protecting group or a pro-drug forming group; $R^3$ is alkyl, heteroalkyl, cycloalkyl, cycloheteroalkyl, arylalkyl, or heteroarylalkyl; Ar is aryl or heteroaryl, each of which is optionally substituted; and wherein the compound is not

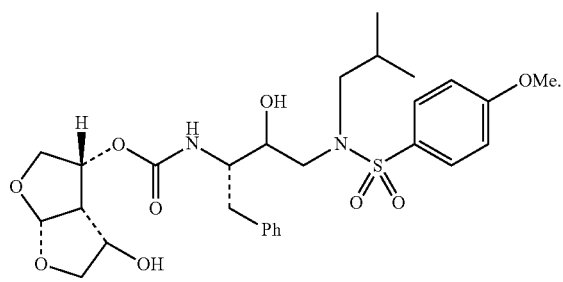

In another embodiment, the compound of the preceding embodiment having the formula

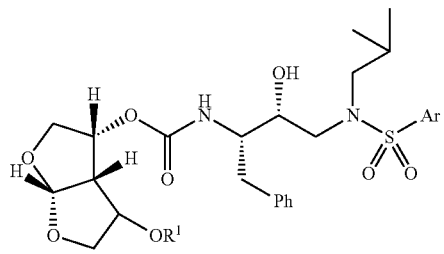

is described, wherein $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; and Ar is aryl or heteroaryl, each of which is optionally substituted.

In another embodiment, compounds of the preceding embodiment wherein Ar is substituted phenyl are described.

It is to be understood that the additional compounds described herein are prepared according to the processes described herein, optionally in conjunction with conventional processes, by the appropriate choice of the starting materials used in the various chemical steps. For example, compounds of Formula (III) where $R^1$ is alkyl other than methyl, substituted alkyl, arylalkyl other than benzyl, substituted arylalkyl, and the like, are prepared according to the process of Scheme 3 where compounds analogous to (9) are converted to compounds analogous to (12) and (13), where R in Scheme 3 is alkyl other than methyl, substituted alkyl, arylalkyl other than benzyl, substituted arylalkyl, and the like.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfinyl or a derivative thereof" includes $SO_2H$ and salts thereof, and esters and amides thereof.

As used herein, the term "sulfonyl or a derivative thereof" includes $SO_3H$ and salts thereof, and esters and amides thereof.

As used herein, the term "phosphinyl or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonyl or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1$-$C_6$ alkyl)($C_1$-$C_6$ alkyl)amino, alkylcarbonylamino, N—$(C_1$-$C_6$ alkyl)alkylcarbonylamino, aminoalkyl, $C_1$-$C_6$ alkylaminoalkyl, $(C_1$-$C_6$ alkyl)($C_1$-$C_6$ alkyl)aminoalkyl, alkylcarbonylaminoalkyl, N—$(C_1$-$C_6$ alkyl)alkylcarbonylaminoalkyl, cyano, and nitro; or $Z^X$ is selected from —$CO_2 R^4$ and —$CONR^5 R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl. In another embodiment, the compounds described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES $^1$H NMR and $^{13}$C NMR spectra were recorded on a Bruker Avance 400. IR spectra were recorded on a Mattson Genesis II FT-IR spectrometer. Optical rotations were recorded on a Perkin-Elmer 341 or an Autopol III autometric polarimeter. Anhydrous solvents were obtained as follow: Tetrahydrofuran and diethyl ether by distillation from sodium and benzophenone; dichloromethane from calcium hydride. All other solvents were reagent grade. All moisture sensitive reactions were carried out in a flame-dried flask under nitrogen atmosphere. Column chromatography was performed with Whatman 240-400 mesh silica gel under low pressure (3-5 psi). Thin layer chromatography was carried out on E. Merck silica gel 60-F-254 plates.

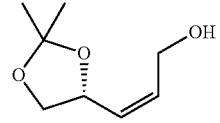

(2Z)-3-((4R)-2,2-Dimethyl-1,3-dioxolan-4-yl)prop-2-en-1-ol (5)

Diisobutyl aluminum hydride (1 M in $CH_2Cl_2$, 27.5 mL, 27.5 mmol,) was slowly added to a cold solution (−78° C.) of ethyl (2Z)-3-[(4R)-2,2-dimethyl-1,3-dioxolan-4-yl]-2-propenoate 4, (2.50 g, 12.5 mmol) in dichloromethane (30 mL). The solution was allowed to stir for 15 min at −78° C. (a color change from colorless to yellow and back to colorless indicates that the reaction is complete). A saturated solution of Rochelle's salt (20 mL) was added and the reaction mixture was warmed to room temperature. The reaction was stirred until both layers were clear. The organic layer was separated and the aqueous layer was extracted with dichloromethane (3×15 mL). The organic layers were combined, washed with brine and dried over $MgSO_4$. The solid was filtered out and the organic layer was concentrated under vacuum. The crude mixture was purified on silica gel using 20% ethyl acetate/hexanes to obtain alcohol 5 (1.9 g, 95% yield) as a colorless oil. $R_f$=0.27 (40% ethyl acetate/hexanes). $^1$H NMR (400 MHz, $CDCl_3$): δ 5.84-5.81 (m, 1H), 5.55 (t, J=8.5 Hz, 1H), 4.85 (q, J=9.6 Hz, 1H), 4.28 (dd, J=6.8, 7.3 Hz, 1H), 4.18 (d, J=4.8 Hz, 1H), 4.08 (t, J=6.5 Hz, 1H), 3.56 (t, J=9.0 Hz, 1H), 2.12 (bs, 1H), 1.41 (s, 3H), 1.38 (s, 3H). $^{13}$C NMR (100 MHz, $CDCl_3$): δ 133.1, 129.4, 109.4, 71.8, 69.4, 58.5, 26.6, 25.8

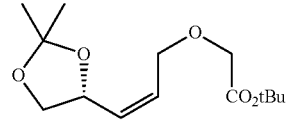 [SMILES: CC(C)(C)OC(=O)COC/C=C\[C@@H]1COC(C)(C)O1]

(2Z)-tert-Butyl 2-(3-((4R)-2,2-dimethyl-1,3-dioxolan-4-yl))allyloxy)acetate (7)$^1$ To a round bottom flask charged with activated molecular sieves (6.0 g) was added a solution of substrate, 6 (4.00 g, 25.3 mmol) in acetonitrile, followed by t-butylbromoacetate (4.48 mL, 30.3 mmol), tetrabutylammonium iodide (1.12 g, 1.45 mmol) and cesium hydroxide monohydrate (5.10 g, 30.3 mmol) at room temperature. The reaction was allowed to stir for 24 h. The solid was filtered out and the solvent was concentrated under vacuum; the residue was purified by flash column chromatography (5% ethyl acetate/hexanes) to afford 7 (5.86 g, 85% yield) as a colorless oil. $R_f$=0.57 (30% ethyl acetate/hexanes). $[\alpha]^{23}_D$=−3.30 (c 1.0, $CH_2Cl_2$); $^1$H NMR (400 MHz, $CDCl_3$): δ 5.78-5.74 (m, 1H), 5.61-5.66 (m, 1H), 4.83 (q, J=7.4 Hz, 1H), 4.16-4.20 (m, 2H), 4.09 (dd, J=6.2, 2.0 Hz, 1H), 3.94 (d, J=3.1 Hz, 2H), 3.54 (t, J=8.1 Hz, 1H), 1.47 (s, 9H), 1.34 (s, 3H), 1.31 (s, 3H). $^{13}$C NMR (100 MHz, $CDCl_3$): δ 169.3, 131.4, 129.5, 109.3, 81.6, 71.9, 69.4, 67.7, 66.5, 28.0, 26.6, 25.8.

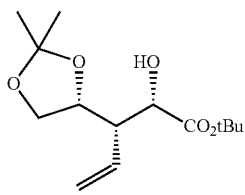 [SMILES: C=C[C@H]([C@@H]1COC(C)(C)O1)[C@H](O)C(=O)OC(C)(C)C]

(2S,3S)-tert-Butyl 3-((4R)-2,2-dimethyl-1,3-dioxolan-4-yl))-2-hydroxypent-4-enoate (9): A solution of 1 M potassium t-butoxide (8.81 mL 8.81 mmol) in THF was added to a cold solution (−10° C.) of 7 (2.00 g, 7.35 mmol) in THF (73 mL) and stirred for 1 h. The reaction was quenched with water (10 mL). The reaction mixture was diluted with ethyl acetate, the organic layer was separated and the aqueous layer was extracted with ethyl acetate (3×15 mL). The organic layers were combined, washed with brine and dry over $MgSO_4$. The solvent was concentrated under vacuum and the residue was purified with a gradient of 5%-10% ethyl acetate/hexanes. The desired rearranged product 9 (1.26 g, 63% yield (17:1 dr)) was obtained as a colorless oil. $R_f$=0.49 (30% ethyl acetate/hexanes). $[\alpha]^{23}_D$=+4.85 (c 1.3, $CH_2Cl_2$); Major product: $^1$H NMR (400 MHz, $CDCl_3$): δ 5.81-5.75 (m, 1H). 5.16 (dd, J=17.1, 10.3 Hz, 2H) 4.28 (q, J=6.4 Hz, 1H),), 4.1 (q, J=2.5 Hz, 1H), 4.05 (t, J=6.2 Hz, 1H), 3.80 (t, J=7.8 Hz, 1H), 3.08 (d, J=4.7 Hz, 1H), 2.57-2.54 (m, 1H), 1.43 (s, 9H), 1.32 (s, 3H), 1.25 (s, 3H). $^{13}$C NMR (100 MHz, $CDCl_3$): δ 172.5, 132.4, 119.6, 109.1, 82.7, 76.0, 71.2, 67.3, 50.3, 27.9, 26.8, 25.4.

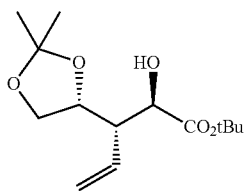 [SMILES: C=C[C@H]([C@@H]1COC(C)(C)O1)[C@@H](O)C(=O)OC(C)(C)C]

(2R,3S)-tert-Butyl 3-((4R)-2,2-dimethyl-1,3-dioxolan-4-yl)-2-hydroxypent-4-enoate: Minor product: $[\alpha]^{23}_D$=−25.2 (c 1.1, $CH_2Cl_2$); $^1$H NMR (400 MHz, $CDCl_3$): δ 5.76-5.86 (m, 1H), 5.20 (dd, J=17.2, 10.3 Hz, 2H), 4.36-4.32 (m, 1H), 4.06-3.99 (m, 2H), 3.70 (t, J=7.9, 1H), 3.0 (d, J=8.2 Hz, 1H), 2.47-2.41 (m, 1H), 1.46 (s, 9H), 1.29 (s, 3H), 1.23 (s, 3H). $^{13}$C NMR (100 MHz, $CDCl_3$): δ 172.6, 133.3, 119.4, 109.0, 82.7, 74.7, 72.3, 67.2, 51.0, 27.9, 26.1, 25.3

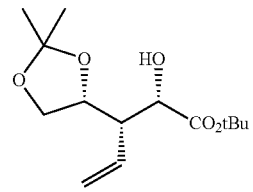 [SMILES: C=C[C@H]([C@@H]1COC(C)(C)O1)[C@H](O)C(=O)OC(C)(C)C]

(2S,3S)-tert-Butyl 3-((4R)-2,2-dimethyl-1,3-dioxolan-4-yl))-2-hydroxypent-4-enoate (9)$^2$: A solution of LiHMDS (18.0 mL 1 M in THF, 18.0 mmol) was added to a cold solution (−45° C.) of 7 (3.60 g, 13.2 mmol) in THF (100 mL) (LiHMDS was added at a rate that did not exceed −40° C.). The reaction mixture was allowed to warm slowly to −30° C. over 1 h. the reaction was quenched with saturated ammonium chloride (10 mL) extracted with ethyl acetate (3×20 mL) after warming to room temperature. The organic layers were combined washed with brine, dry over anhydrous $MgSO_4$ and reduce under vacuum. The residue was purified with a 5-10 percent gradient of ethyl acetate/hexanes. The desired rearranged product 9 (3.00 g, 83% yield) was obtained as a colorless oil. The spectral data was identical to the product obtained with potassium t-butoxide.

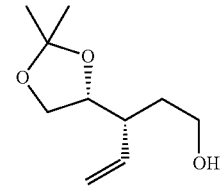

(3R)-3-(4R)-2,2-Dimethyl-1,3-dioxolan-4-yl)pent-4-en-1-ol (10): To a cold (−20° C.) THF (25 mL) solution of 9 (2.00 g, 7.35 mmol) was added triethyl amine (3.00 mL, 22.1 mmol) followed by MsCl (0.68 mL, 8.81 mmol). The reaction was stirred for 2 h. The reaction was quenched with saturated ammonium chloride (10 mL) then extracted with ethyl acetate (3×15 mL). The organic layers were combined and dried over anhydrous $MgSO_4$. The solvent was concentrated under vacuum and the crude mixture was purified using 10% ethyl acetate/hexanes to obtain the desired mesylated compound (2.40 g, 93% yield) as a colorless oil. $R_f$=0.41 (30% ethyl acetate/hexanes). $^1$H NMR (400 MHz, $CDCl_3$): δ 5.84-5.75 (m, 1H), 5.24 (dd, J=17.2, 10.3 Hz, 2H), 4.97 (d, J=3.1 Hz, 1H), 4.22 (q, J=4.7 Hz, 1H), 4.09 (t, J=6.2 Hz, 1H), 3.78 (t, J=8.0 Hz, 1H), 3.07 (s, 3H), 2.79-2.74 (m, 1H), 1.46 (s, 9H), 1.33 (s, 3H), 1.26 (s, 3H). $^{13}$C NMR (100 MHz, $CDCl_3$): δ 166.6, 131.3, 120.8, 109.4, 83.6, 78.1, 74.9, 66.9, 49.1, 39.2, 27.9, 26.4, 25.2.

The mesylated compound above was dissolved (632 mg, 1.80 mmol) in THF (10 mL) at 0° C. was added lithium aluminum hydride (288 mg, 7.20 mmol). The reaction was stirred for 30 min at 0° C. then stirred for 6 h at room temperature. (A small aliquot of the reaction was quenched and checked by NMR to determine the reaction's progress). The reaction was cooled to 0° C. and diluted with ethyl acetate. This was followed by the stepwise addition of 3N NaOH (0.5 mL) and $H_2O$ (1 mL). The reaction was stirred until a white precipitate formed. $MgSO_4$ was added to the solution and the white solid was filtered out. The solvent was removed under vacuum and the crude was purified by flash column chromatography (gradient 10%-20% ethyl acetate/hexanes) to give 10 (270 mg, 80% yield) as a colorless oil. $R_f$=0.27 (40% ethyl acetate/hexanes). $[\alpha]^{23}_D$=−47.51 (c 1.0, CH$_2$Cl$_2$); $^1$H NMR (400 MHz, CDCl$_3$): δ 5.71-5.64 (m, 1H), 5.12 (dd, J=15.7, 10.3 Hz, 2H), 4.08 (q, J=6.9 Hz, 1H), 3.98 (t, J=6.3 Hz, 1H), 3.71-3.61 (m, 3H), 2.33 (m, 1H), 1.98 (bs, 1H), 1.69-1.60 (m, 2H), 1.33 (s, 3H), 1.26 (s, 3H). $^{13}$C NMR (100 MHz, CDCl$_3$): δ 137.3, 117.6, 108.9, 78.1, 67.1, 60.2, 43.6, 33.7, 26.2, 25.2

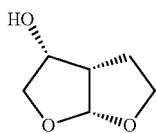

(3R,3aS,6aR)-Hexahydrofuro[2,3-b]furan-3-ol (11): Into a cold a solution of 10 (2.60 g, 14.0 mmol) in CH$_2$Cl$_2$/MeOH (50 mL, 4:1 at −78° C.) was bubbled a stream of ozone until a blue color persisted. The ozone stream was stopped and a stream of argon was bubbled through the reaction mixture to remove the excess ozone. Dimethyl sulfide (5.02 mL, 69.8 mmol) was added to the reaction and the mixture was warmed to room temperature and stirred an additional 3 h. The reaction mixture was carefully concentrated at (0° C.) to remove any excess of dimethyl sulfide, then, 20 mL of CHCl$_3$, p-TsOH (90.0 mg, 0.473 mmol) and MeOH (0.5 μL) were added to the residue and the mixture was refluxed for 1 h. The reaction was again carefully concentrated and the residue was purified on silica gel (20% ether/hexanes to 40% ether/hexanes) to afford compound 11, (1.45 g, 80% yield) as a colorless oil. R$_f$=0.2 (60% ethyl acetate/hexanes). $[\alpha]^{23}_D$=−13.2 (c 1.0, MeOH); $^1$H NMR (400 MHz, CDCl$_3$): δ 5.67 (d, J=5.1 Hz, 1H), 4.45-4.42 (m, 1H), 3.92-3.99 (m, 2H), 3.89-3.85 (m, 1H), 3.62 (dd, J=9.1, 7.0 Hz, 1H), 2.87-2.83 (m, 1H), 2.33-2.27 (m, 1H), 2.22 (d, J=5.1 Hz, 1H), 1.81-1.91 (m, 1H). $^{13}$C NMR (100 MHz, CDCl$_3$): δ 109.4, 73.0, 70.8, 69.8, 46.5, 24.8.

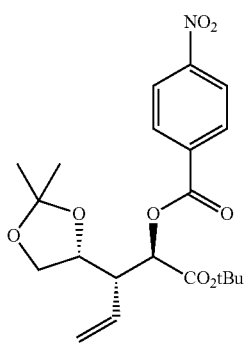 [SMILES: C=C[C@H]([C@@H]1COC(C)(C)O1)[C@@H](OC(=O)c1ccc([N+](=O)[O-])cc1)C(=O)OC(C)(C)C]

(2S,3R)-1-tert-Butoxy-3-((4R)-2,2-dimethyl-1,3-dioxolan-4-yl)-1-oxopent-4-en-2-yl-4-nitrobenzoate (16)[3]: Into a cold (0° C.) solution of 9 (0.29 g, 1.06 mmol) in THF (10 mL) was added triphenylphosphine (1.12 g, 4.25 mmol) p-nitrophenylbenzoic acid (0.71 g, 4.25 mmol) and diethyl azodicarboxylate (0.74 g, 4.25 mmol). The reaction was allowed to stir 24 h. The reaction was diluted with ethyl acetate (10 mL) and quenched with a saturated solution of sodium bicarbonate (10 mL). The reaction was extracted with ethyl acetate (3×15 ml). The organic layers were combined, washed with brine and dried over anhydrous sodium sulfate. The solvent was concentrated under vacuum and the crude mixture was purified on silica gel using 5% ethyl acetate/hexanes to obtain 17 (0.390 g, 87%) as a pale yellow solid. R$_f$=0.24 (10% ethyl acetate/hexanes). $[\alpha]^{D}_{23}$=+2.3 (c 1.0, CHCl$_3$). $^1$H NMR (400 MHz, CDCl$_3$): δ 8.25 (d, J=15.6, 2H), 8.22 (d, J=15.6, 2H), 5.83-5.57 (m, 1H), 5.30 (dd, 17.2, 10.3 Hz, 2H), 5.11 (d, J=7.3 Hz, 1H), 4.43 (q, J=2.2 Hz, 1H), 4.09 (t, J=6.34 Hz, 1H), 3.78 (t, 8.00 Hz, 1H), 2.80-2.79 (m, 1H), 1.45 (s, 9H), 1.41 (s, 3H), 1.30 (s, 3H). $^{13}$C NMR (100 MHz, CDCl$_3$): δ 167.5, 163.9, 150.7, 134.8, 131.8, 130.9, 123.5, 120.5, 109.3, 83.0, 74.6, 73.9, 48.5, 27.9, 26.1, 25.2

Removal of Benzoate Ester and General Procedures for O-Methylation:

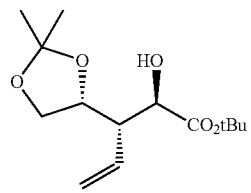 [SMILES: C=C[C@H]([C@@H]1COC(C)(C)O1)[C@@H](O)C(=O)OC(C)(C)C]

(2R,3S)-tert-Butyl-3-((4R)-2,2-dimethyl-1,3-dioxolan-4-yl)-2-hydroxypent-4-enoate: To a cold (0° C.) solution of 16 (0.39 g, 0.93 mmol) in methanol was added potassium carbonate (0.256 g, 1.85 mmol). The reaction was allowed to stir for 0.5 h. The reaction was quenched with a saturated ammonium chloride (5.0 mL) and the methanol was removed under vacuum. The solution was extracted with ethyl acetate (3×10 mL) and the combined organic layer was combined, washed with brine and dried over anhydrous sodium sulfate. The solvent was removed under vacuum and the residue was purified on silica gel using 10% ethyl acetate/hexanes to obtain the free secondary alcohol (0.226 mg, 90% yield) as a white solid. R$_f$=0.38 (30% ethyl acetate/hexanes). $[\alpha]^{D}_{23}$=−25.2 (c 1.0, CHCl$_3$). $^1$H NMR (400 MHz, CDCl$_3$); δ 5.85-5.78 (m, 1H), 5.21 (dd, J=17.3, 10.3 Hz, 2H), 4.36-4.34 (m, 1H), 4.08-4.00 (m, 2H), 3.71 (t, J=7.73 Hz, 1H), 2.97 (d, J=8.1 Hz, 1H), 2.48-2.43 (m, 1H), 1.47 (s, 9H), 1.42 (s, 3H), 1.34 (s, 3H). $^{13}$C NMR (100 MHz, CDCl$_3$): δ 172.6, 133.3, 119.0, 109.0, 82.7, 74.8, 72.3, 67.2, 51.0, 27.9, 26.1, 25.3

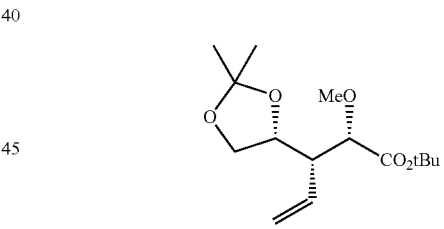

(2S,3R)-tert-Butyl 3-((4R)-2,2-Dimethyl-1,3-dioxolan-4-yl)-2-methoxypent-4-enoate (12): To a cold (0° C.) solution of 9 (0.20 g, 0.73 mmol) and methyl iodide (0.092 mL) in THF (5 mL) was added sodium hydride (0.023 g, 0.96 mmol). The reaction was allowed to stir for 2 h at 23° C. then quenched with saturated ammonium chloride (5 mL). The reaction mixture was extracted with ethyl acetate (3×10 mL). The organic layers were combined, washed with brine and dried over anhydrous sodium sulfate. The solvent was reduced under vacuum and the residue was purified on silica gel to obtain 12 (0.19 g, 90% yield) as a colorless oil. R$_f$=0.62 (30% ethyl acetate/hexanes). $[\alpha]^{D}_{23}$=−31.2 (c 1.0, CHCl$_3$). $^1$H NMR (400 MHz, CDCl$_3$): δ 5.81-5.75 (m, 1H), 5.13 (dd, 17.1, 10.3, 2H), 4.2 (q, J=7.0 Hz, 1H), 3.98 (dd, J=6.1, 2.0 Hz, 1H), 3.79 (t, J=3.79 Hz, 2H), 3.33 (s, 3H), 2.61-2.56 (m, 1H), 1.43 (s, 9H), 1.38 (s, 3H), 1.32 (s, 3H) $^{13}$C NMR (100 MHz, CDCl$_3$): δ 169.9, 133.3, 119.1, 108.8, 81.6, 80.9, 75.5, 67.2, 58.3, 49.8, 28.0, 26.5, 25.4

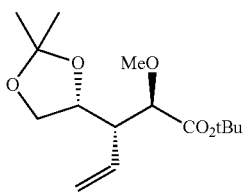 [SMILES: C=C[C@H]([C@@H]1COC(C)(C)O1)[C@@H](OC)C(=O)OC(C)(C)C]

(2R,3R)-tert-Butyl 3-((4R)-2,2-dimethyl-1,3-dioxolan-4-yl)-2-methoxypent-4-enoate (17): Follow the general procedure outlined for compound 12. $R_f$=0.7 (30% ethyl acetate/hexanes). $[\alpha]_{23}^D$=−22.4 (c 1.0, CHCl$_3$). $^1$H NMR (400 MHz, CDCl$_3$): δ 5.75-5.22 (m, 1H), 5.16 (dd, J=17.2, 10.3 Hz, 2H), 4.40-4.36 (m, 1H), 4.00 (t, J=6.8 Hz, 1H), 3.65 (m, 2H), 3.37 (s, 3H), 2.44-2.38 (m, 1H), 1.45 (s, 9H), 1.38 (s, 3H), 1.34 (s, 3H). $^{13}$C NMR (100 MHz, CDCl$_3$): δ 170.5, 132.2, 120.1, 108.6, 81.9, 81.7, 73.9, 67.2, 57.9, 50.1, 28.0, 26.1, 25.3

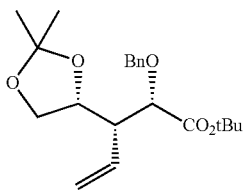 [SMILES: C=C[C@H]([C@@H]1COC(C)(C)O1)[C@H](OCc1ccccc1)C(=O)OC(C)(C)C]

(2S,3R)-tert-Butyl 2-(benzyloxy)-3-(R)-2,2-dimethyl-1,3-dioxolan-4-yl)pent-4-enoate (13): To a cold (0° C.) solution of 9 (0.20 g, 0.73 mmol), benzyl bromide (0.178 mL, 1.47 mmol) tetrabutyl ammonium bromide (0.027 g, 0.073 mmol) in THF (5.0 mL) was added sodium hydride (0.023 g, 0.95 mmol). The reaction was allowed to stir for 2 h at 23° C. and then quenched with saturated ammonium chloride (5 mL). The reaction was extracted with ethyl acetate (3×10 mL). The organic layers were combined, washed with brine and dried over anhydrous sodium sulfate. The solvent was reduced under vacuum and the residue was purified on silica gel to obtain 13 (0.263 g, 99% yield) as a colorless oil. $R_f$=0.61 (20% ethyl acetate/hexanes). $[\alpha]_{23}^D$=−36.8 (c 1.0, CHCl$_3$). $^1$H NMR (400 MHz, CDCl$_3$): δ 7.35-7.29 (m, 5H), 5.95-5.85 (m, 1H), 5.18 (dd, J=17.2, 10.3 Hz, 2H) 4.75 (d, J=11.5 Hz, 1H), 4.33 (d. J=11.5 Hz, 1H), 4.20 (q, J=7.3, 1H), 3.85 (d, J=3.5 Hz, 1H), 3.77 (dd, J=6.1, 2.0 Hz, 1H), 3.66 (t, J=7.7 Hz, 1H), 2.64-2.58 (m, 1H), 1.47 (s, 9H), 1.39 (s, 3H), 1.33 (s, 3H). $^{13}$C NMR (100 MHz, CDCl$_3$): δ 169.9, 137.3, 133.5, 128.3, 128.2, 127.9, 119.1, 108.9, 81.7, 78.2, 75.6, 72.3, 67.2, 50.3, 28.1, 26.6, 25.4

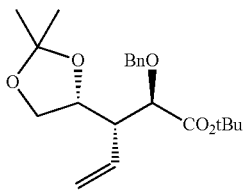 [SMILES: C=C[C@H]([C@@H]1COC(C)(C)O1)[C@@H](OCc1ccccc1)C(=O)OC(C)(C)C]

(2R,3R)-tert-Butyl 2-(Benzyloxy)-3-((4R)-2,2-dimethyl-1,3-dioxolan-4-yl)pent-4-enoate (18): Follow the procedure outlined for compound 13. $R_f$=0.58 (20% ethyl acetate/hexanes). $[\alpha]_{23}^D$=+32.3 (c 1.0, CHCl$_3$). $^1$H NMR (400 MHz, CDCl$_3$): δ 7.35-7.29 (m, 5H), 5.76-5.71 (m, 1H), 5.73 (dd, J=17.2, 10.3 Hz, 2H), 4.62 (d, J=11.5 Hz, 1H), 4.44 (d, J=11.5 Hz, 1H), 3.98 (t, J=6.4 Hz, 1H), 3.88 (d, J=9.5 Hz, 1H), 3.65 (t, J=7.9 Hz, 1H), 2.54-2.51 (m, 1H), 1.44 (s, 9H), 1.37 (s, 3H), 1.34 (s, 3H)

$^{13}$C NMR (100 MHz, CDCl$_3$): δ 170.5, 137.3, 132.2, 128.3, 128.0, 127.8, 120.1, 108.5, 81.7, 79.8, 73.9, 72.3, 67.2, 49.9, 28.0, 26.1, 25.3

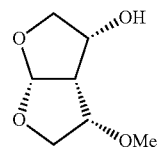

(3R,3aR,4S,6aS)-4-Methoxyhexahydrofuro[2,3-b]furan-3-ol (14): To a cold (0° C.) solution of 12 (0.10 mg, 0.349 mmol) in THF (5 mL) was added lithium aluminum hydride (0.028 mg, 0.733 mmol). The reaction was allowed to stir for 1 h at 23° C. after which the reaction was cooled to 0° C. and quenched by adding excess ethyl acetate, 1 N NaOH (0.5 mL), H$_2$O (0.5 mL). After a white precipitate formed magnesium sulfate was added and stirred for 15 min. The reaction mixture was filtered and concentrated under vacuum.

The crude mixture was taken up in DCM/MeOH (5 ml, 4:1) and a stream of O$_3$ was bubble through the solution until a blue color persisted. Argon was bubbled through the blue solution until the solution became clear. Dimethyl sulfide (0.13 mL, 1.75 mmol) was added to the reaction and the mixture was warmed to room temperature and stirred an additional 3 h. The reaction mixture was carefully concentrated at (0° C.) to remove any excess of dimethyl sulfide, then, 5 mL of CH$_2$Cl$_2$, p-TsOH (6.0 mg, 0.037 mmol) and MeOH (0.5 μL) were added to the residue and the mixture was stirred for 2 h at room temperature. The reaction was again carefully concentrated and the residue was purified on silica gel (20% ether/hexanes to 50% ether/hexanes) to afford compound 14, (0.03 g, 54% yield 2 steps) as a colorless oil. $R_f$=0.20 (60% ethyl acetate/hexanes). $[\alpha]_{23}^D$=−35.9 (c 1.1, CHCl$_3$). $^1$H NMR (400 MHz, CDCl$_3$): δ 5.59 (d, J=5.5 Hz, 1H), 4.51 (m, 1H), 4.25 (m, 2H), 4.09 (dd, J=5.9, 6.0 Hz, 1H), 3.97-3.89 (m, 3H), 3.43 (s, 3H), 2.91-2.85 (m, 1H) $^{13}$C NMR (100 MHz, CDCl$_3$): δ 108.8, 82.9, 74.2, 73.7, 70.9, 58.1, 46.5

(3R,3aR,4R,6aS)-4-Methoxyhexahydrofuro[2,3-b]furan-3-ol (19): Follow the general procedure outlined for compound 14.

$R_f$=0.26 (60% ethyl acetate/hexanes). $^1$H NMR (400 MHz, CDCl$_3$): δ5.74 (d, J=5.2 Hz, 1H), 4.51-4.46 (m, 1H), 4.23 (d, J=3.5 Hz 1H), 4.03 (d, J=10.2 Hz 1H), 3.96-3.91 (m, 2H), 3.55 (dd, J=6.7, 6.8 Hz, 1H), 3.29 (s, 3H), 2.95 (bs, 1H), 2.81 (dd, J=5.25, 5.4 Hz). $^{13}$C NMR (100 MHz, CDCl$_3$): δ 109.1, 80.67, 73.7, 73.3, 69.6, 56.4, 52.9

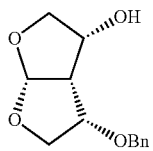

(3R,3aR,4S,6aS)-4-(Benzyloxy)hexahydrofuro[2,3-b]furan-3-ol (15): Follow the general procedure outlined for compound 14.

$R_f$=0.43 (60% ethyl acetate/hexanes). $[\alpha]_{23}^D$=−22.9 (c 0.8, CHCl$_3$). $^1$H NMR (400 MHz, CDCl$_3$): δ 7.38-7.32-(m, 5H), 5.59 (d, J=5.5 Hz, 1H), 4.66 (d, 11.5 Hz, 1H), 4.55 (d, 11.5 Hz, 1H), 4.48-4.44 (m, 2H), 4.28 (d, J=6.3 Hz, 1H), 4.11 (dd, J=6.8, 2.3 Hz, 1H), 3.97-3.92-(m, 3H), 2.88-2.83 (m, 1H). $^{13}$C NMR (100 MHz, CDCl$_3$): δ 136.4, 128.7, 128.5, 127.9, 108.7, 80.8, 74.4, 73.7, 73.2, 71.2, 46.6

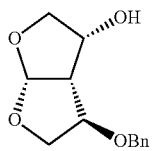

(3R,3aR,4R,6aS)-4-(Benzyloxy)hexahydrofuro[2,3-b]furan-3-ol (20): Follow the general procedure outlined for compound 14.

$R_f$=0.52 (60% ethyl acetate/hexanes). $[\alpha]_{23}^D$=+ 58.6 (c 1.1, CHCl$_3$). $^1$H NMR (400 MHz, CDCl$_3$): δ 7.38-7.29 (m, 5H), 5.82 (d, J=5.3 Hz, 1H), 4.56-4.46 (m, 4H), 4.12 (d, J=10.2 Hz, 1H), 4.03-3.96 (m, 2H) 3.61-3.57 (dd, J=6.9, 6.8 Hz, 1H), 2.91 (dd, J=5.3, 5.4 Hz, 1H), 2.16 (bs, 1H). $^{13}$C NMR (100 MHz, CDCl$_3$): δ 137.7, 128.4, 127.7, 127.7, 109.2, 78.6, 74.2, 73.2, 71.1, 68.9, 55.4

Preparation of Activated Carbonates from Polycyclic P2-Ligands: 15, 16, 21, 22

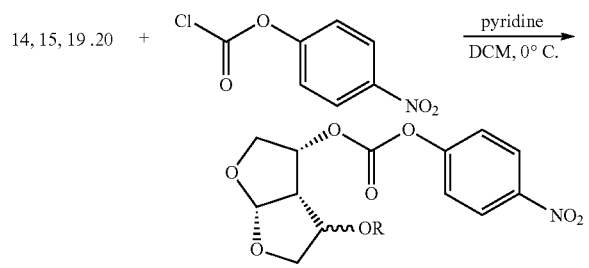

21a-d

To a solution of the corresponding ligand (14, 15, 19, and 20) in dry CH$_2$Cl$_2$ was added pyridine (2.30 eq). The resulting mixture was cooled to 0° C. under argon and 4-nitrophenyl-chloroformate (2.20 eq) was added in one portion. The resulting mixture was stirred at 0° C. until completion. The reaction mixture was evaporated to dryness and the residue was purified by flash column chromatography on silica gel using a gradient of 20-40% ethyl acetate/hexanes to afford the desired ligand-activated carbonate 21a-d.

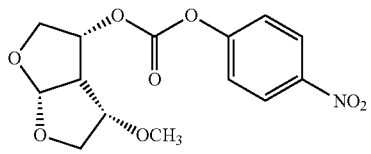

(3R,3aR,4S,6aR)-4-Methoxyhexahydrofuro[2,3-b]furan-3-yl 4-nitrophenyl carbonate (21a): The reaction mixture was purified on silica gel using 40% ethyl acetate/hexanes. The desired activated alcohol was obtained as a white solid (33 mg, 80% yield). $R_f$=0.12 (60% ethyl acetate/hexanes). $^1$H NMR (400 MHz, CDCl$_3$): δ 8.27 (d, J=10.3 Hz, 2H), 7.35 (d, J=10.3 Hz, 2H), 5.72 (d, J=5.1 Hz, 1H), 5.57-5.34 (m, 1H), 4.29-4.19 (m, 2H), 4.1-4.01 (m, 3H), 3.38 (s, 3H), 3.12-3.07 (m, 1H). $^{13}$C NMR (100 MHz, CDCl$_3$): δ 155.5, 152.1, 145.4, 125.2, 121.8, 108.6, 81.1, 77.4, 73.2, 70.7, 59.0, 46.2

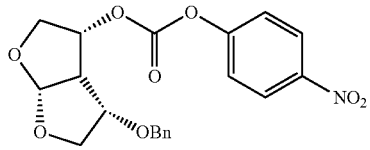

(3R,3aR,4S,6aR)-4-(Benzyloxy)hexahydrofuro[2,3-b]furan-3-yl 4-nitrophenyl carbonate (21b): The reaction mixture was purified on silica gel using 20% ethyl acetate/hexanes. The desired activated alcohol was obtained as a white solid (41 mg, 80% yield). $R_f$=0.42 (40% ethyl acetate/hexanes). $^1$H NMR (400 MHz, CDCl$_3$): δ 8.08 (d, J=7.1 Hz, 2H), 7.30 (bs, 5H), 6.95 (d, J=7.1 Hz, 2H), 5.71 (d, J=5.2 Hz, 1H), 5.61-5.58 (m, 1H), 4.41 (d, J=11.2 Hz, 1H), 4.52 (d, J=11.2 Hz, 1H), 4.42 (q, J=7.6 Hz, 1H), 4.29 (dd, J=2.7, 10.4 Hz, 1H), 4.13-4.07 (m, 3H), 3.11-3.06 (m, 1H). $^{13}$C NMR (100 MHz, CDCl$_3$): δ 155.3, 152.0, 145.1, 137.1, 128.4, 128.1, 127.9, 124.9, 121.7, 108.5, 79.3, 77.5, 73.7, 73.4, 70.8, 46.7

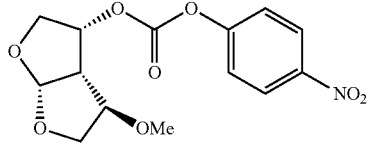 [SMILES: CO[C@H]1CO[C@@H]2OC[C@H](OC(=O)Oc3ccc([N+](=O)[O-])cc3)[C@@H]21]

(3R,3aS,4S,6aR)-4-Methoxyhexahydrofuro[2,3-b]furan-3-yl 4-nitrophenyl carbonate (21c): The reaction mixture was purified on silica gel using 30% ethyl acetate/hexanes. The desired activated alcohol was obtained as a white solid (49 mg, 80% yield). $R_f$=0.15 (30% ethyl acetate/hexanes). $^1$H NMR (400 MHz, CDCl$_3$): δ 8.29 (d, J=9.9 Hz, 2H), 7.38 (d, J=10.2, 2H), 5.87 (d, J=5.2 Hz, 1H), 5.32-5.37 (m, 1H), 4.17-4.12 (m, 3H), 4.10 (dd, J=3.8, 5.6 Hz. 1H), 3.91 (dd, J=5.57, 5.57 Hz, 1H), 3.34 (s, 3H), 3.13-3.10 (m, 1H). $^{13}$C NMR (100 MHz, CDCl$_3$): δ 155.0, 151.8, 145.6, 125.3, 121.5, 108.8, 80.8, 77.3, 73.5, 70.6, 56.6, 51.1

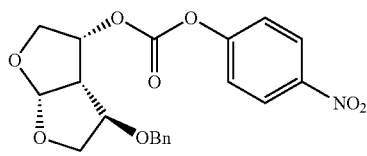 [SMILES: O=C(Oc1ccc([N+](=O)[O-])cc1)O[C@H]1CO[C@H]2OC[C@H](OCc3ccccc3)[C@H]21]

(3R,3aS,4R,6aR)-4-Methoxyhexahydrofuro[2,3-b]furan-3-yl 4-nitrophenyl carbonate (21d): The reaction mixture was purified on silica gel using 20% ethyl acetate/hexanes. The desired activated alcohol was obtained as a white solid (51 mg, 89% yield). $R_f$=0.30 (30% ethyl acetate/hexanes). $^1$H NMR (400 MHz, CDCl$_3$): δ 8.28 (d, J=9.9 Hz, 2H), 7.34-7.27 (m, 7H), 5.91 (d, J=4.0 Hz, 1H), 5.29-5.37 (m, 1H), 4.55 (s, 3H), 4.30 (J=3.5 Hz, 1H), 4.20-4.14 (m, 2H), 4.08 (dd, J=3.7, 3.8 Hz, 1H), 3.92 (dd, J=5.7, 5.7 Hz, 1H), 3.20 (dd, J=5.1, 5.2 Hz, 1H). $^{13}$C NMR (100 MHz, CDCl$_3$): δ 154.9, 151.7, 145.5, 137.2, 128.5, 127.9, 127.5, 125.3, 121.5, 108.9, 78.5, 76.4, 74.0, 70.9, 70.4, 51.5

General Procedure for the Synthesis of HIV-1-Protease Inhibitors:

Isostere 22 was taken up in CH$_3$CN and cooled to 0° C. DIEA (i-Pr$_2$EtN) (5 eq, excess) was added, and the resulting solution was stirred for 5 min. A solution of the corresponding activated bis-THF ligand (14, 15, 19 and 20) in THF was added via cannula and the resulting solution was stirred at room temperature for 24 h to 3 days or until the reaction was complete. The solution was evaporated to dryness and the crude residue purified by flash column chromatography on silica gel to yield the desired inhibitor.

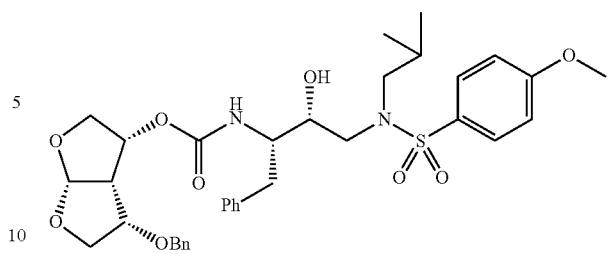

(3R,3aS,4S,6aR)-4-(benzyloxy)hexahydrofuro[2,3-b]furan-3-yl-(2S,3R)-3-hydroxy-4-(N-isobutyl-4-methoxyphenylsulfonamido)-1-phenylbutan-2-ylcarbamate, 23b: The reaction mixture was purified on silica gel using 40% ethyl acetate/hexanes. The desired inhibitor was obtained as a white solid (25 mg, 71% yield). $[\alpha]_{23}^D$=+ 62.0, $R_f$=0.26 (50% ethyl acetate/hexanes). $^1$H NMR (400 MHz, CDCl$_3$): δ 7.68 (d, J=8.9 Hz, 2H), 7.36-7.13 (m, 10H), 6.97 (d, J=8.9 Hz, 2H), 5.62 (d, J=5.3, 1H), 5.46-5.40 (m, 1H), 4.72 (d, J=9.0, 1H), 4.44 (q, J=11.8, 2H), 4.26 (d, J=7.8, 1H), 4.07 (dd, J=9.9, 3.0, 1H), 3.98-3.88 (m, 3H), 3.86 (s, 3H), 3.82-3.69 (m, 2H), 3.66 (ddd, J=8.6, 6.0, 2.9, 1H), 3.09 (dd, J=15.2, 8.8, 1H), 2.96-2.83 (m, 4H), 2.73 (dd, J=13.4, 6.6, 1H), 2.56 (dd, J=13.9, 5.1, 1H), 1.82-1.55 (m, 1H), 0.87 (d, J=6.6, 3H), 0.83 (d, J=6.6, 3H). $^{13}$C NMR (100 MHz, CDCl$_3$): δ 162.9, 155.6, 137.5, 136.9, 129.8, 129.7, 129.4, 128.4, 127.9, 125.5, 114.2, 108.7, 78.3, 74.0, 73.1, 73.0, 71.6, 71.4, 58.6, 55.5, 54.3, 53.6, 46.8, 34.9, 27.1, 20.1, 19.7.

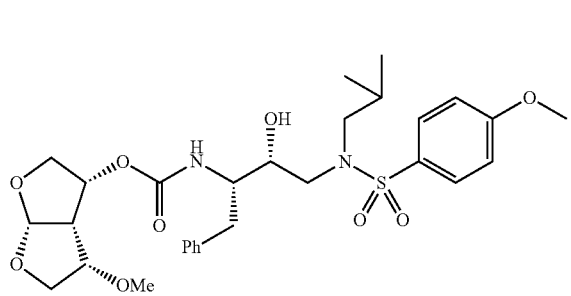 [SMILES: COc1ccc(S(=O)(=O)N(CC(C)C)C[C@@H](O)[C@H](Cc2ccccc2)NC(=O)O[C@H]2CO[C@H]3OC[C@@H](OCc4ccccc4)[C@H]32)cc1]

(3R,3aS,4S,6aR)-4-methoxyhexahydrofuro[2,3-b]furan-3-yl-(2S,3R)-3-hydroxy-4-(N-isobutyl-4-methoxyphenylsulfonamido)-1-phenylbutan-2-ylcarbamate, 23a: The reaction mixture was purified on silica gel using 40% ethyl acetate/hexanes. The desired inhibitor was obtained as a white solid (20 mg, 55% yield). $R_f$=0.12 (60% ethyl acetate/hexanes). $^1$H NMR (400 MHz, CDCl$_3$): δ 7.69 (d, J=8.8, 2H), 7.34-7.13 (m, 6H), 6.97 (d, J=8.9, 2H), 5.63 (d, J=5.3, 1H), 5.44-5.37 (m, 1H), 4.88 (d, J=8.9, 1H), 4.13-3.74 (m, 9H), 3.20 (s, 3H), 3.15-2.82 (m, 7H), 2.77 (dd, J=13.4, 6.8, 1H), 1.85-1.70 (m, 1H), 0.88 (d, J=6.6, 3H), 0.84 (t, J=5.6, 3H). $^{13}$C NMR (100 MHz, CDCl$_3$): δ 163.0, 155.7, 137.1, 129.8, 129.6, 129.4, 128.4, 126.5, 114.2, 109.0, 80.7, 73.8, 72.9, 71.9, 71.3, 58.6, 58.5, 55.6, 54.6, 53.6, 46.4, 35.3, 27.1, 20.1, 19.7

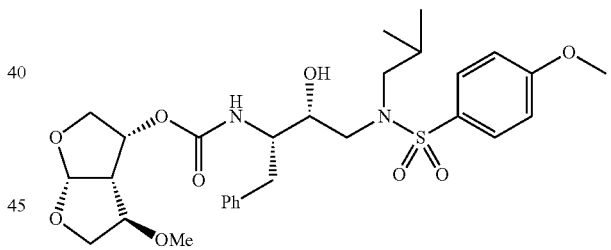

(3R,3aS,4R,6aR)-4-methoxyhexahydrofuro[2,3-b]furan-3-yl-(2S,3R)-3-hydroxy-4-(N-isobutyl-4-methoxyphenylsulfonamido)-1-phenylbutan-2-ylcarbamate, 23c: The reaction mixture was purified on silica gel using 40% ethyl acetate/hexanes. The desired inhibitor was obtained as a white solid (28 mg, 77% yield). $[\alpha]_{23}^D$=+ 7.0, $R_f$=0.14 (50% ethyl acetate/hexanes). $^1$H NMR (400 MHz, CDCl$_3$): δ δ 7.71 (d, J=8.8, 2H), 7.32-7.18 (m, 5H), 6.98 (d, J=8.8, 2H), 5.74 (d, J=5.2, 1H), 5.10 (dd, J=21.2, 8.6, 2H), 4.00-3.82 (m, 7H), 3.77 (dd, J=10.1, 3.7, 1H), 3.69 (dd, J=9.8, 5.6, 2H), 3.41 (d, J=3.3, 1H), 3.22-3.03 (m, 5H), 3.03-2.85 (m, 3H), 2.81 (dd, J=13.5, 6.8, 2H), 1.84 (s, 1H), 0.92 (d, J=6.6, 3H), 0.88 (d, J=6.6, 3H). $^{13}$C NMR (100 MHz, CDCl$_3$): δ 163.1, 155.2, 137.6, 129.6, 129.4, 129.2, 128.5, 126.6, 114.3, 108.9, 80.9, 73.9, 72.8, 72.3, 71.0, 58.7, 56.2, 55.6, 55.3, 53.6, 51.0, 35.4, 27.2, 20.12, 19.88.

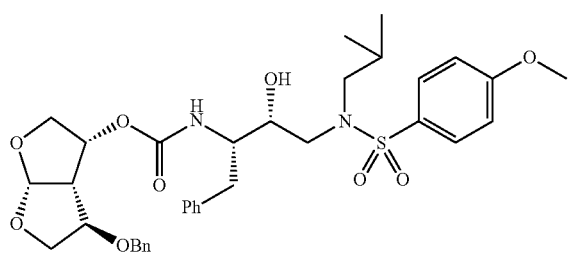 [SMILES: COc1ccc(S(=O)(=O)N(CC(C)C)C[C@@H](O)[C@H](Cc2ccccc2)NC(=O)O[C@H]2CO[C@H]3OC[C@H](OCc4ccccc4)[C@H]32)cc1]

(3R,3aS,4R,6aR)-4-(benzyloxy)hexahydrofuro[2,3-b]furan-3-yl-(2S,3R)-3-hydroxy-4-(N-isobutyl-4-methoxyphenylsulfonamido)-1-phenylbutan-2-ylcarbamate, 23d: The reaction mixture was purified on silica gel using 40% ethyl acetate/hexanes. The desired inhibitor was obtained as a white solid (48 mg, 96% yield). $[\alpha]_{23}^D$=+ 25.0, $R_f$=0.20 (40% ethyl acetate/hexanes). $^1$H NMR (400 MHz, CDCl$_3$): δ 7.70 (d, J=7.1, 2H), 7.37-7.13 (m, 10H), 6.98 (d, J=8.9, 2H), 5.79 (d, J=5.2, 1H), 5.15-5.08 (m, 1H), 4.95 (d, J=8.6, 1H), 4.37 (d, J=11.8, 1H), 4.27 (d, J=11.8, 1H), 4.07-3.91 (m, 2H), 3.91-3.79 (m, 6H), 3.70 (dd, J=10.3, 4.1, 3H), 3.15 (dd, J=15.2, 8.4, 1H), 2.98 (ddd, J=16.4, 13.0, 7.7, 4H), 2.85-2.72 (m, 2H), 1.81 (dd, J=14.0, 6.9, 1H), 0.92 (d, J=6.6, 3H), 0.86 (t, J=11.0, 3H). $^{13}$C NMR (100 MHz, CDCl$_3$): δ 163.1, 155.2, 137.7, 137.5, 129.6, 129.4, 129.3, 128.5, 128.3, 127.7, 127.4, 126.6, 114.3, 109.0, 79.2, 74.3, 72.7, 72.4, 71.1, 70.8, 58.7, 55.6, 55.2, 53.6, 51.6, 35.4, 27.2, 20.1, 19.8.

TABLE 3

Enzymatic inhibitory and antiviral activity of inhibitors containing bis-THF derivatives

| Entry | Inhibitor | $K_i$ (nM) | IC$_{50}$ (nM)$^{a,b}$ |
|---|---|---|---|
| 1. | 3a (TMC-126)[22] | 0.014 | 1.4 |
| 2. | 23a | 0.035 | 56 |
| 3. | 23b | 0.073 | 335 |
| 4. | 23c | 0.0029 | 2.4 |

TABLE 3-continued

Enzymatic inhibitory and antiviral activity of inhibitors containing bis-THF derivatives

| Entry | Inhibitor | $K_i$ (nM) | $IC_{50}$ (nM)[a,b] |
|---|---|---|---|
| 5. | 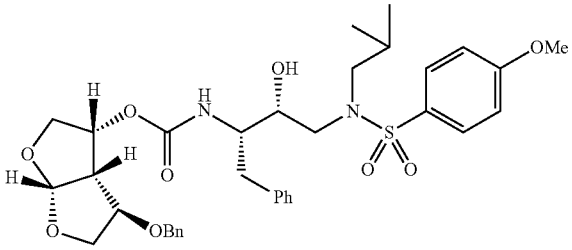<br>23d | 0.3 | — |

[a]Values are means of at least three experiments.
[b]Human T-lymphoid (MT-2) cells were exposed to 100 TCID50 values of HIV-1LAI and cultured in the presence of each PI, and $IC_{50}$ values were determined using the MTT assay.

While certain embodiments of the present invention have been described and/or exemplified above, it is contemplated that considerable variation and modification thereof are possible. Accordingly, the present invention is not limited to the particular embodiments described and/or exemplified herein.

What is claimed is:

1. A compound having the formula

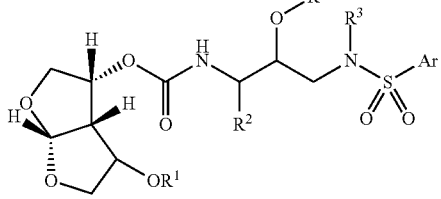

wherein $R^1$ is hydrogen or an OH protecting group, or is selected from the group consisting of alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, and heteroarylalkyl, each of which is optionally substituted; $R^2$ is alkyl, cycloalkyl, heteroalkyl, cycloheteroalkyl, arylalkyl, or heteroalkyl, each of which is optionally substituted; $R^{P2}$ is hydrogen, hydroxyl protecting group or a pro-drug forming group; $R^3$ is alkyl, heteroalkyl, cycloalkyl, cycloheteroalkyl, arylalkyl, or heteroarylalkyl; Ar is aryl is optionally substituted with a radical $—(CH_2)_xZ^x$, where x is an integer from 0-6 and $Z^x$ is selected from halogen, hydroxy, alkanoyloxy, optionally substituted aroyloxy, alkyl, alkoxy, cycloalkyl, cycloalkoxy, alkenyl, alkynyl, haloalkyl, haloalkoxy, halocycloalkyl, halocycloalkoxy, $C_1$-$C_6$alkylamino, $(C_1$-$C_6$alkyl)$(C_1$-$C_6$alkyl)amino, alkylcarbonylamino, N—$(C_1$-$C_6$alkyl)alkylcarbonylamino, aminoalkyl, $C_1$-$C_6$alkylaminoalkyl, $(C_1$-$C_6$alkyl)$(C_1$-$C_6$alky)aminoalkyl, alkylcarbonylaminoalkyl, N—$(C_1$-$C_6$alkyl)alkylcarbonylaminoalkyl, cyano, and nitro or $Z^x$ is selected from —$CO_2R^4$ and —$CONR^5R^6$, where $R^4$, $R^5$, and $R^6$ are each independently selected in each occurrence from hydrogen, $C_1$-$C_6$alkyl, aryl-$C_1$-$C_6$alkyl, and heteroaryl-$C_1$-$C_6$alkyl; or Ar is 3,4-methylenedioxyphenyl; or Ar is heteroaryl which is optionally substituted; and wherein the compound is not

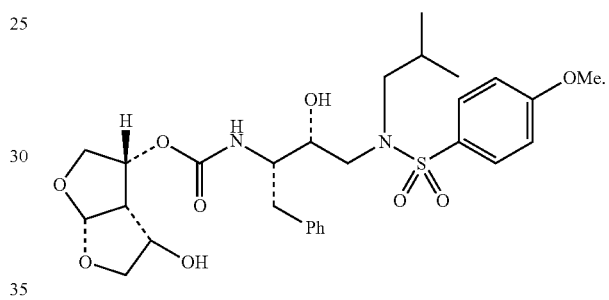

2. The compound of claim 1 which is

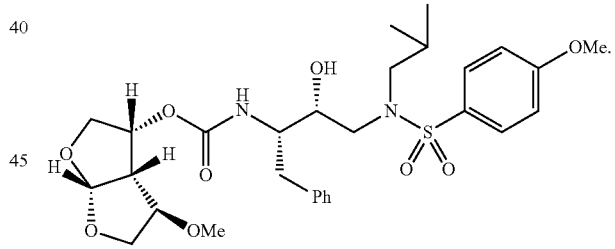

3. The compound of claim 1 wherein $R^2$ is arylalkyl.
4. The compound of claim 3 wherein $R^2$ is benzyl.
5. The compound of claim 1 wherein $R^3$ is branched alkyl.
6. The compound of claim 5 wherein $R^3$ is iso-butyl.
7. The compound of claim 1 wherein $R^{P2}$ is hydrogen.
8. The compound of claim 1 wherein Ar is substituted phenyl.
9. The compound of claim 1 wherein $R^1$ is alkyl or arylalkyl.
10. The compound of claim 9 wherein $R^1$ is methyl or benzyl.
11. The compound of claim 1 wherein Ar is phenyl substituted on the 4 position with OMe, $CH_2OMe$ or Ar is 3,4-methylenedioxyphenyl.
12. The compound of claim 1 wherein Ar is phenyl substituted on the 4 position with OMe, $CH_2OMe$, or Ar is 3,4-methylenedioxyphenyl; $R^1$ is methyl or benzyl; $R^2$ is arylalkyl; R is branched alkyl; and $R^{P2}$ is hydrogen.

13. The compound of claim 12 wherein $R^1$ is methyl; $R^2$ is benzyl; and $R^3$ is iso-butyl.

14. A pharmaceutical composition comprising the compound of claim 1; and one or more carriers, diluents, or excipients, or a combination thereof.

15. A method of treating a patient in need of relief from HIV infection comprising the step of administering to the patient a therapeutically effective amount of the compound of claim 1.

16. A pharmaceutical composition comprising the compound of claim 2; and one or more carriers, diluents, or excipients, or a combination thereof.

17. A method of treating a patient in need of relief from HIV infection comprising the step of administering to the patient a therapeutically effective amount of the compound of claim 2.

* * * * *